US005799054A

United States Patent [19]
Hum et al.

[11] Patent Number: 5,799,054
[45] Date of Patent: Aug. 25, 1998

[54] METHODS AND APPARATUS FOR STABILIZING A GANTRY IN A COMPUTED TOMOGRAPHY SYSTEM

[75] Inventors: Russell Wayne Hum, Waukesha; Thomas Robert Murray, Delafied; Shawn Patrick Faessler, Waukesha, all of Wis.

[73] Assignee: General Electric Company, Milwaukee, Wis.

[21] Appl. No.: 777,417

[22] Filed: Dec. 31, 1996

[51] Int. Cl.⁶ .................................. A61B 6/02
[52] U.S. Cl. ............................... 378/17; 378/4
[58] Field of Search ........................ 378/4, 15, 17, 378/19, 204

[56] References Cited
U.S. PATENT DOCUMENTS
4,935,949  6/1990  Fujita et al. .................. 378/4

*Primary Examiner*—David P. Porta
*Attorney, Agent, or Firm*—John S. Beulick; John H. Pilarski

[57] ABSTRACT

The present invention, in one form, is a brake assembly for a tilting gantry. The brake assembly is coupled to the gantry in substantially the same manner as a driving actuator is connected to the gantry, and includes a hydraulic cylinder, a piston, a reservoir and a valve. The cylinder includes a first end, a second end, and a sidewall extending between the first end and the second end to define a chamber. The piston includes a head and an arm which is configured to couple to the gantry. The piston is positioned within the hydraulic cylinder so that the head of the piston is in the cylinder chamber and the piston arm extends through a piston opening of the first end of the hydraulic cylinder. The reservoir is configured to retain hydraulic fluid, and the valve is connected in series circuit between the hydraulic cylinder and the reservoir. Particularly, a fluid line couples the reservoir to the hydraulic cylinder, and the valve is positioned in the fluid line to control the flow of hydraulic fluid between the reservoir and the hydraulic cylinder.

20 Claims, 3 Drawing Sheets

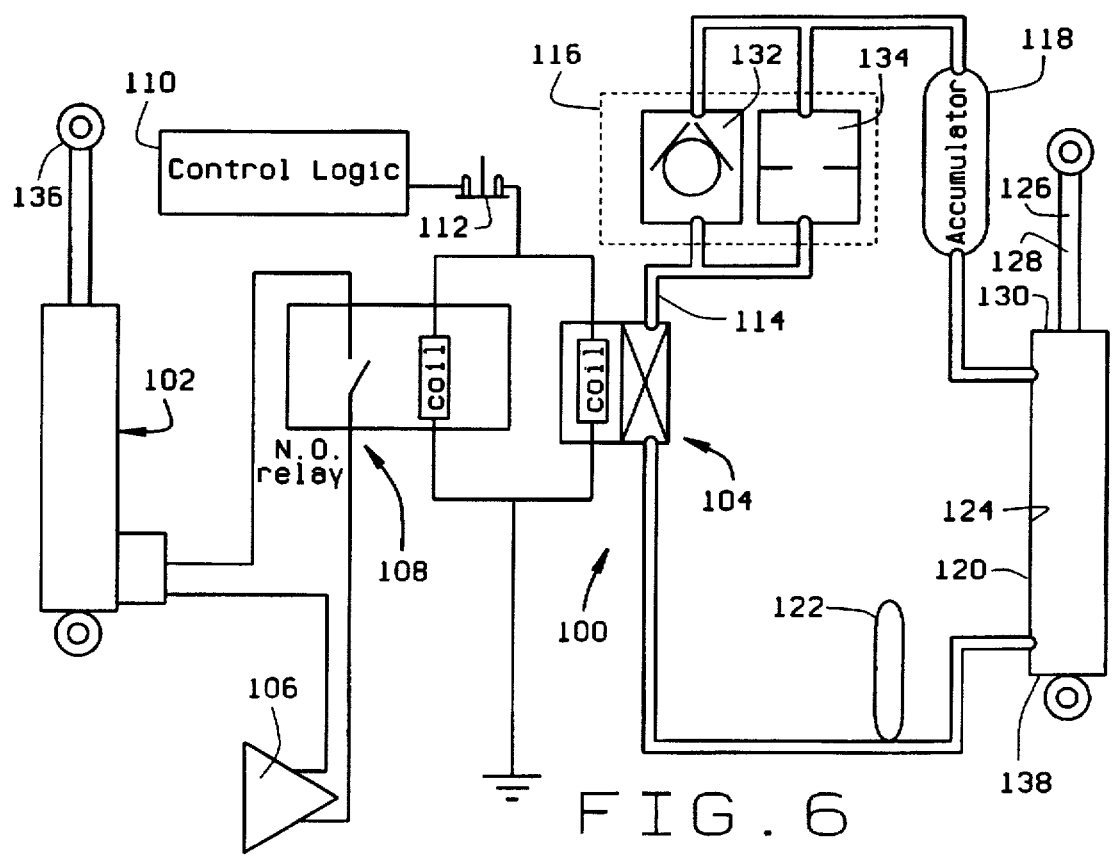
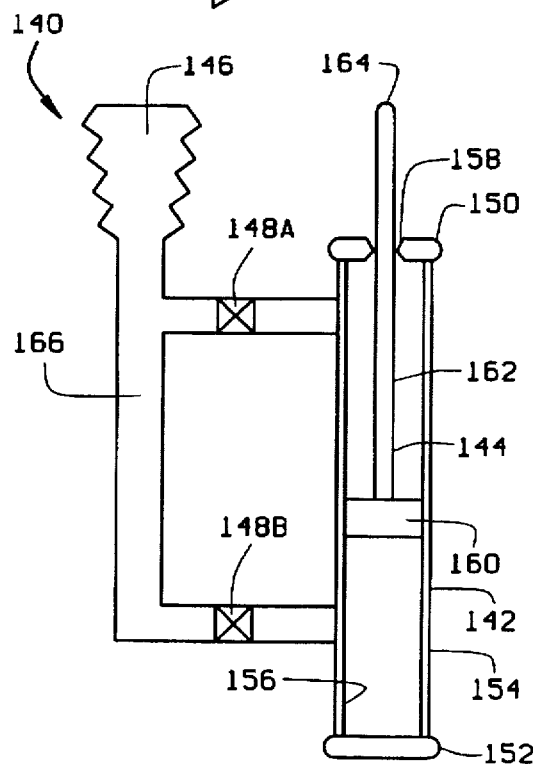
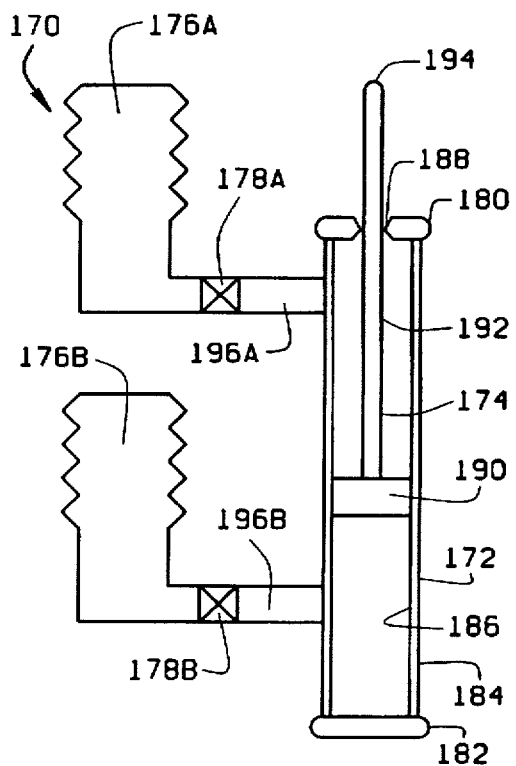
FIG. 6
FIG. 7
FIG. 8

METHODS AND APPARATUS FOR STABILIZING A GANTRY IN A COMPUTED TOMOGRAPHY SYSTEM

FIELD OF THE INVENTION

This invention relates generally to computed tomography systems, and more particularly, to stabilizing a gantry when performing a scan using a computed tomography system.

BACKGROUND OF THE INVENTION

In at least one known CT system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile of the object.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles during one revolution of the x-ray source and detector. In an axial scan, the projection data is processed to construct an image that corresponds to a two dimensional slice taken through the object.

One method for reconstructing an image from a set of projection data is referred to in the art as the filtered backprojection technique. This process converts the attenuation measurements from a scan into integers called "CT numbers" or "Hounsfield units", which are used to control the brightness of a corresponding pixel on a cathode ray tube display.

Image slices typically are acquired so that each slice is perpendicular to a longitudinal axis of the patient, i.e., the slices are substantially parallel to each other and spaced in the z direction. However, it often is preferable to acquire slices at an orientation other than the perpendicular orientation to better visualize certain structures within the patient. For example, slices at angles other than 90 degrees to the longitudinal axis of the patient, i.e., non-transverse slices, are preferable when studying certain internal organs.

To provide such an angular orientation, a driving mechanism typically is used to tilt the gantry so the axis of x-ray source rotation is inclined relative to the axis of the patient. The driving mechanism includes an actuator which is coupled to the gantry. The actuator, which typically either is hydraulic or electric, drives the gantry about a pivot point so that the gantry may be positioned at different tilt angles. An encoder or some other transducer is coupled to the gantry to detect the tilt angle. If an encoder is used, the amount of gantry tilt about the pivot point, and generates pulses indicative of the angular orientation (theta) of the gantry about the pivot point. The output of the tilt transducer is coupled to a control processor which is programmed to control operation of the imaging machine.

In operation, the gantry typically is initially positioned substantially perpendicular to the longitudinal axis of the patient. The driving mechanism then drives the gantry about the pivot point so that the gantry moves angularly with respect to the patient. As the angular orientation of the gantry changes, the encoder generates pulses indicative of such angular orientation. The pulses, as explained above, are supplied to the control processor. The pulses may be stored in an accumulator, and the accumulated pulse count is utilized to position the gantry at the desired angle, or tilt angle.

After positioning the gantry at the desired tilt angle, the driving mechanism stops driving the gantry, and the driving mechanism is utilized to stabilize the gantry at the desired tilt angle. The gantry exerts significant force on the driving mechanism both while the mechanism drives and stabilizes the gantry. In addition, and because the driving mechanism is not coupled to the gantry at the center of gantry rotation, the rotational forces generated by the rotating x-ray source and detector array may cause the gantry to sway.

To stabilize the gantry at the desired tilt angle and reduce the gantry force exerted on the driving mechanism, known CT systems utilize a braking drive. The braking drive typically is either an electric or a hydraulic drive, and is coupled to the gantry in substantially the same manner in which the driving mechanism is coupled to the gantry. When the driving mechanism has tilted the gantry to the desired position, the braking drive is actuated to maintain the gantry at such position. Accordingly, the braking drive cooperates with the driving mechanism to reduce the force of the gantry exerted on the driving mechanism. While known braking drives are generally reliable, such drives are expensive.

It would be desirable, therefore, to stabilize the gantry at the selected tilt angle without using hydraulic or electric braking drives. It also would be desirable to achieve satisfactory gantry stability while reducing the costs for the imaging system.

SUMMARY OF THE INVENTION

These and other objects may be attained by a system which, in one embodiment, utilizes a hydraulic brake assembly to easily and quickly stabilize a gantry. In accordance with one embodiment of the present invention, the hydraulic brake assembly includes a hydraulic cylinder, a piston, a reservoir and a valve. The piston includes a piston head and an arm, and is positioned within the hydraulic cylinder so that the piston head is in the cylinder chamber and the piston arm extends through an opening at a first end of the hydraulic cylinder. The piston arm is coupled to the gantry. The reservoir is configured to retain hydraulic fluid, and the valve is connected in series circuit between the hydraulic cylinder and the reservoir. Particularly, a fluid line couples the reservoir to the hydraulic cylinder, and the valve is positioned in the fluid line to control the flow of hydraulic fluid between the reservoir and the hydraulic cylinder. The hydraulic brake assembly is coupled to the gantry in substantially the same manner in which known gantry tilt driving mechanisms are coupled to the gantry.

In operation, a gantry tilt drive mechanism drives the gantry to a desired tilt angle. While tilting the gantry, the brake assembly valve is in an open position so that hydraulic fluid flows between the reservoir and the hydraulic cylinder chamber. Accordingly, the piston head moves between the first and second ends of the hydraulic cylinder as the piston arm moves with the tilting gantry. Upon attaining the desired tilt angle, the hydraulic brake assembly is actuated to stabilize the gantry at the desired tilt angle. Particularly, the brake assembly valve is closed to prevent hydraulic fluid from flowing between the reservoir and the hydraulic cylinder chamber, thus substantially preventing the piston head from moving between the first and second ends of the hydraulic cylinder. By locking the piston head in place, the piston arm coupled to the gantry provides stability, and serves as a brake, to secure the gantry at the selected tilt angle.

In addition, the brake assembly serves as a mechanism to assist in changing/replacing the tilt drive mechanism. Particularly, the brake assembly maintains the gantry in position during drive replacement. The brake assembly also acts as a safety device in the event of tilt drive failure.

The above-described brake assembly is simple and inexpensive to construct and install on known imaging systems. Such assembly also provides a cost-effective method for reducing gantry sway.

BRIEF DESCRIPTION OF THE DRAWINGS

FIG. 6 is a schematic illustration of the hydraulic brake assembly shown in FIG. 3 coupled to a gantry in accordance with another embodiment of the present invention.

FIG. 7 is a schematic illustration of a hydraulic brake assembly in accordance with another embodiment of the present invention.

FIG. 8 is a schematic illustration of a hydraulic brake assembly in accordance with yet another embodiment of the present invention.

DETAILED DESCRIPTION OF THE DRAWINGS

Figure 1:
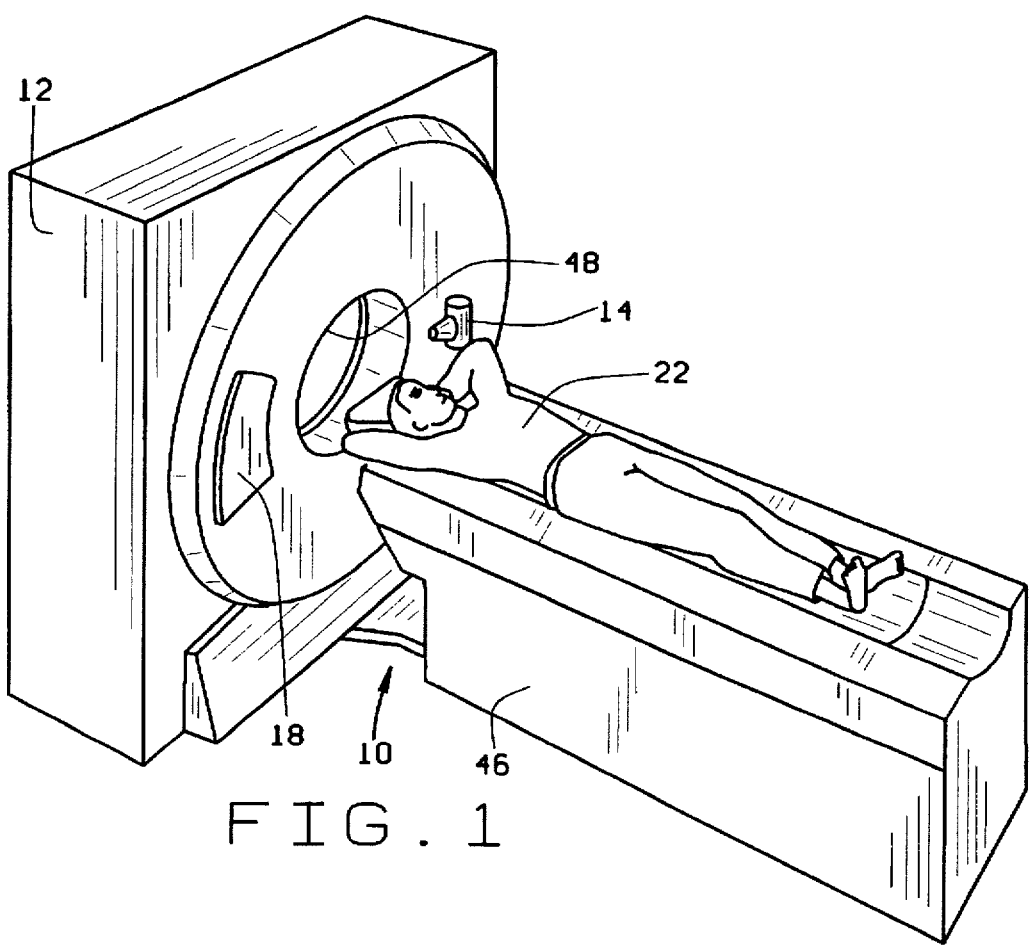
FIG. 1 is a pictorial view of a CT imaging system.
Figure 2:
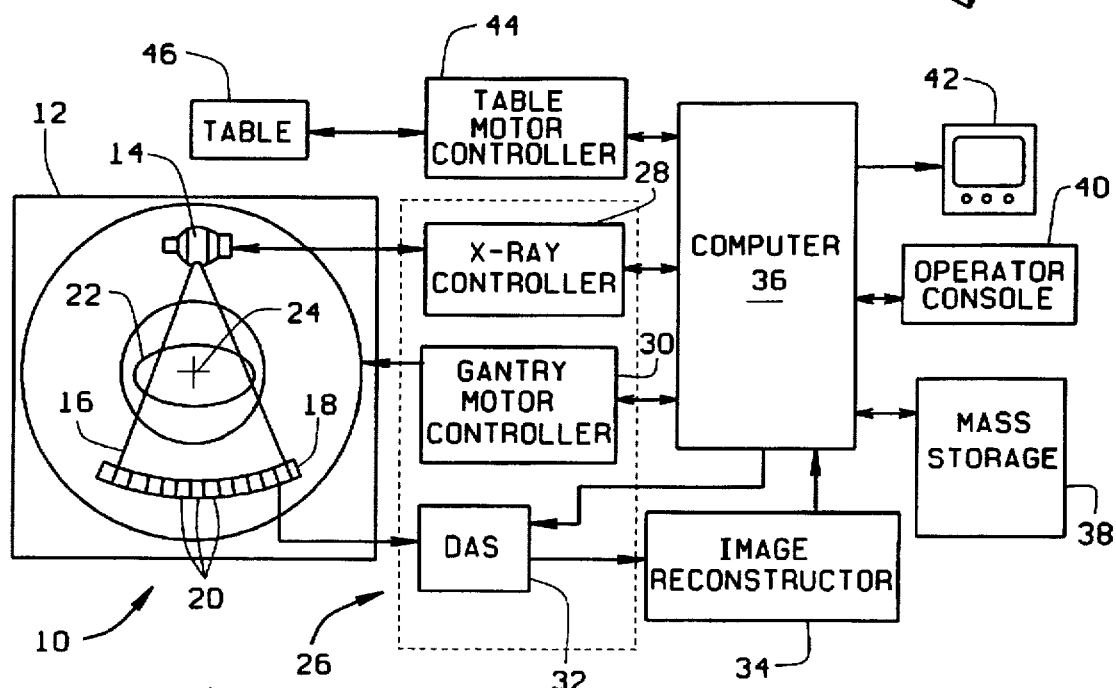
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through a medical patient 22. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

During a scan, gantry 12 often is tilted with respect to the z-axis. A driving mechanism (not shown) tilts gantry 12 about a pivot point (not shown) so that an axis of gantry rotation (not shown) is not parallel to the x-axis. An encoder (not shown) is coupled to the gantry to detect the tilt angle, i.e., the amount of gantry tilt about the pivot point, and generates pulses indicative of the angular orientation (theta) of the gantry about the pivot point. The output of the encoder is coupled, for example, to computer 36 or gantry motor controller 30.

The driving mechanism includes an electric actuator which has a driving portion and an actuating arm which extends from the driving portion. The actuating arm is coupled to gantry 12 and the driving portion is coupled to a stationary gantry support. When the electric actuator is activated, the actuating arm either extends or retracts to tilt gantry 12 about the pivot point, and the encoder transmits tilting position signals to computer 36. Electric actuators for tilting gantries are well known in the art. Similarly, coupling an electric actuator to a gantry is well known.

Figures 3, 4:
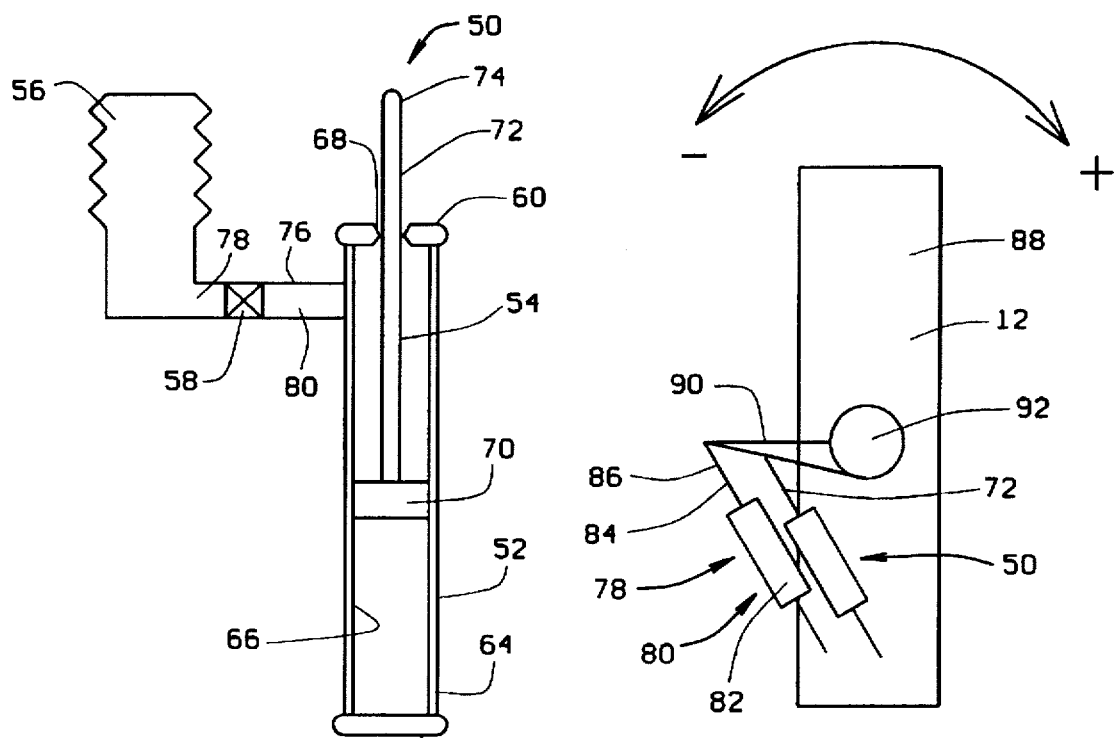
FIG. 3 is a schematic illustration of a hydraulic brake assembly in accordance with one embodiment of the present invention.
FIG. 4 is a schematic illustration of the hydraulic brake assembly shown in FIG. 3.

FIG. 3 is a side elevation view of a hydraulic brake assembly 50 in accordance with one embodiment of the present invention. Hydraulic brake assembly 50 includes a hydraulic cylinder 52, a piston 54, a reservoir 56 and a valve 58. Hydraulic cylinder 52 includes a first end 60, a second end 62, and a sidewall 64 extending between first end 60 and second end 62 to define a chamber 66. First end 60 of hydraulic cylinder 52 includes a sealed opening 68.

Piston 54 includes a piston head 70 and an arm 72 extending from piston head 70. One end 74 of piston arm 72 is configured to couple to gantry 12. Piston 54 is positioned in hydraulic cylinder 52 so that piston arm 72 extends substantially coaxially with hydraulic cylinder 52. More particularly, piston head 70 has a substantially cylindrical geometric shape and is positioned in chamber 66 so that piston arm 72 extends through opening 68 in hydraulic cylinder first end 60. Piston arm 72 is coupled to a gantry 12 (FIG. 1).

Reservoir 56 is configured to retain a hydraulic fluid, and a fluid line 76 couples reservoir 56 to hydraulic cylinder 52. Particularly, hydraulic fluid through fluid line 76 between reservoir 56 and hydraulic cylinder 52. Valve 58 is connected in series circuit between reservoir 56 and hydraulic cylinder 52 for controlling the flow of hydraulic fluid between reservoir 56 and hydraulic cylinder 52. Valve 58 is configured to alternate between an open position and a closed position. When valve 58 is in the open position, hydraulic fluid flows between reservoir 56 and cylinder chamber 66. When valve 58 is in the closed position, however, closed valve 58 substantially prevents hydraulic fluid from flowing between reservoir 56 and hydraulic cylinder chamber 66.

FIG. 4 is a side view schematic illustration of hydraulic brake assembly 50 and a driving mechanism 78 coupled to gantry 12 in accordance with one embodiment of the present invention. Driving mechanism 78 includes an electric actuator 80 having a cylinder 82 and a piston 84. Electric actuator piston 84 is positioned in cylinder 82 so that a piston arm 86 extends from cylinder 82 and is coupled to gantry 12. Particularly, actuator piston arm 86 is coupled to a first side 88 of gantry 12. An arm 90 extends from a pivot point 92 at first side 88 of gantry 12, and piston arm 84 is coupled to arm 90 so that piston arm 84 rotates gantry 12 about pivot point 92. Electric actuators are well known.

Brake assembly 50 also is coupled to gantry 12. As shown in FIG. 4, piston arm 72 of brake assembly 50 is coupled to first side 88 of gantry 12. More specifically, brake assembly piston arm 72 is coupled to arm 90 so that piston arm 72 is substantially adjacent actuator piston arm 86.

In operation, and to tilt gantry 12, driving mechanism 78 is actuated so that actuator piston arm 86 moves relative to actuator cylinder 82 and tilts gantry 12 about pivot point 92. While actuator piston arm 86 is moving, i.e., extending or retracting from cylinder 82, valve 58 is open so that hydraulic fluid flows between reservoir 56 and hydraulic cylinder chamber 66 (FIG. 3). Accordingly, and while hydraulic fluid flows between reservoir 56 and hydraulic cylinder chamber 66, brake assembly piston head 70 moves between first and second ends 60 and 62, respectively, of hydraulic cylinder 52, and piston arm 72 moves with tilting gantry 12. Particularly, brake assembly piston arm 72 extends and retracts with moving actuator piston arm 86.

After gantry 12 has tilted to the selected tilt angle, valve 58 is closed to prevent hydraulic fluid from flowing between reservoir 56 and hydraulic cylinder chamber 66. Accordingly, brake assembly piston head 70 is substantially prevented from moving between first and second ends 60 and 62, respectively, of hydraulic cylinder 52. More specifically, piston head 70 is locked into place, and piston 54 and cylinder 52 thus serve as a brake to secure gantry 12 at the selected gantry tilt angle.

The above-described brake assembly 50 is inexpensive to fabricate and simple to install on existing CT systems. Furthermore, such brake assembly 50 stabilizes the gantry without using a braking drive.

Brake assembly 50 also may be used to substantially prevent gantry sway. For example, and referring to FIG. 5, which is a schematic illustration of hydraulic brake assembly 50 coupled to gantry 12 in accordance with another embodiment of the present invention, brake assembly 50 is coupled to one side 94 of gantry opening 48 and electric actuator 80 is coupled to an opposite side 96 of gantry opening 48. Particularly, electric actuator piston arm 86 is coupled to side 96 of gantry opening 48 and brake assembly piston arm 72 is coupled to opposite side 94 of gantry opening 48. Accordingly, and when brake assembly piston head 70 is locked into place, brake assembly 50 and electric actuator 80 cooperate to reduce gantry sway between opposite sides 94 and 96, respectively, and thus to stabilize gantry 12.

It is to be understood that such brake assembly may be implemented by several different embodiments. For example, FIG. 6 is a schematic illustration of a hydraulic brake assembly 100 and an electric actuator 102, or a driving mechanism, in accordance with one embodiment of the present invention. Electric actuator 102 is electrically coupled to brake assembly 100. Particularly, electric actuator 102 is electrically coupled to a valve 104, which is a solenoid controlled valve. An electric power drive amplifier 106 is electrically connected in series circuit with a normally open relay 108, or contactor, to drive electric actuator 102 and tilt gantry 12 (FIG. 1). Control logic 110 is electrically coupled both to normally open relay 108 and to valve 104. Control logic 110 is configured to close normally open relay 108 and substantially simultaneously open valve 104, and to open normally open relay 108 and substantially simultaneously close valve 104. An Emergency Off switch 112 is electrically coupled between control logic 110 and valve 104 and is configured to open normally open relay 108 and substantially simultaneously close valve 104. Drive amplifiers, relays, Emergency Off switches, and solenoid valves are well known in the art.

Valve 104 controls the flow of hydraulic fluid within fluid line 114. Particularly, valve 104 is hydraulically connected in series circuit connection with a flow limiter 116, an accumulator 118, a hydraulic cylinder 120, and a shock arrestor 122. Hydraulic cylinder 120, as described above, includes a hydraulic chamber 124, and a piston 126 is positioned in chamber 124 so that a piston arm 128 extends from a sealed end 130 of hydraulic cylinder 120. Accumulator 118 is configured to retain hydraulic fluid and shock arrestor 122 is configured to prevent a "water hammer" in hydraulic fluid when valve 104 closes and interrupts hydraulic fluid flow. Accumulators and shock arrestors are well known.

A pressure sensor may be placed in the fluid line at the exit of the accumulator to sense pressure in the line. In the event of a failure in the system, the pressure in the fluid line would be outside a predetermined acceptable pressure range. The output of the sensor would be provided to the control unit which would open the solenoid valve and stop tilt actuation in the event an out-of-range pressure is sensed.

Flow limiter 116 includes a check valve 132 for limiting hydraulic fluid flow through fluid line 114. Particularly, between valve 104 and hydraulic cylinder 120, fluid line 114 includes an inner fluid line 134, or orifice, which is concentrically positioned in and substantially coextensive with fluid line 114. Depending on the direction of flow of hydraulic fluid between valve 104 and hydraulic cylinder 120, check valve 132 either restricts hydraulic fluid flow to inner fluid line 134 or check valve 132 substantially circumvents inner fluid line 134 to facilitate hydraulic fluid flow through both inner fluid line 134 and through fluid line 114 between a perimeter of fluid line 114 and a perimeter of inner fluid line 134.

Figure 5:
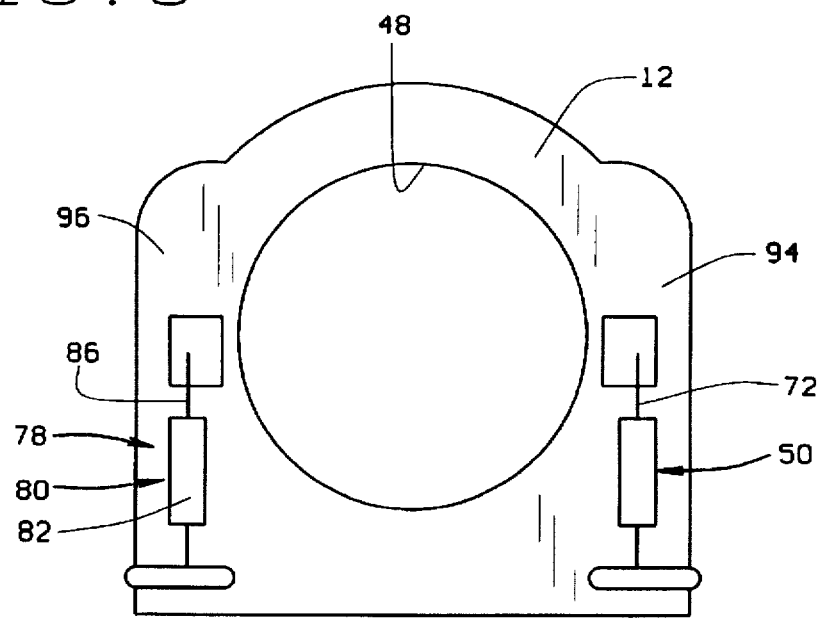
FIG. 5 is a schematic illustration of the hydraulic brake assembly shown in FIG. 3 coupled to a gantry in accordance with one embodiment of the present invention.

In operation, an actuating arm 136 of electric actuator 102 is coupled to gantry 12 and piston arm 128 of brake assembly 100 also is coupled to gantry 12. Actuating arm 102 and piston arm 128 may be coupled either to the same side of gantry opening 48 (FIG. 4) or to opposite sides of gantry opening 48 (FIG. 5). To tilt gantry 12, control logic 110 closes normally open relay 108 so that drive amplifier 106 drives electric actuating arm 136 and tilts gantry 12 about a pivot point. Particularly, to tilt gantry 12 in a positive direction (FIG. 4), actuating arm 136 is extended, and to tilt gantry 12 in a negative direction (FIG. 4), actuating arm 136 is retracted.

While tilting gantry 12, i.e., when normally open relay 108 is closed, control logic 110 opens valve 104 so that hydraulic fluid flows through fluid line 114. Accordingly, hydraulic fluid flows both into and out of hydraulic cylinder chamber 124 so that piston 126 may move in chamber 124 relative to first and second ends 130 and 138 respectively, of hydraulic cylinder 120. Particularly, a piston head of piston 126 moves between hydraulic cylinder first and second ends 130 and 138, respectively, so that piston arm 128 extends or retracts with electric actuating arm 136. While actuating arm 136 extends, i.e., tilts gantry 12 in the positive direction, check valve 132 substantially circumvents inner fluid line 134 to facilitate hydraulic fluid flow through fluid line 114 and piston 126 movement relative to chamber 124. When actuating arm 136 retracts, however, check valve 132 restricts fluid flow so that hydraulic fluid flows only through inner fluid line 134. Different amounts of hydraulic fluid are retained in chamber 124 for different lengths of piston arm 128 extension, and accumulator 118 retains the hydraulic fluid difference for various extensions of piston arm 128.

After gantry 12 has tilted to the desired tilt angle, or when Emergency Off switch 120 is activated, control logic 110 opens normally open relay 108 and closes valve 104. Hydraulic fluid flow thus is interrupted within fluid line 114, and piston 126 ceases movement relative to chamber 124. In addition, shock arrestor 122 activates to prevent a "water hammer" effect in hydraulic fluid remaining in fluid line 114. Accordingly, hydraulic cylinder 120, piston 128, and hydraulic fluid within chamber 124 serve as a brake to prevent any further gantry 12 tilt and to secure gantry 12 at the selected tilt angle.

The above-described brake assembly implementation is simple and inexpensive to construct and install on known imaging systems. Such implementation also provides a cost-effective method for reducing gantry sway.

FIG. 7 is a side elevation view of a hydraulic brake assembly 140 in accordance with another embodiment of the present invention. Brake assembly 140 includes a hydraulic cylinder 142, a piston 144, a reservoir 146 and two valves 148A and 148B. Hydraulic cylinder 142 includes a first end 150, a second end 152, and a sidewall 154 extending between first end 150 and second end 152 to define a chamber 156. First end 150 of hydraulic cylinder 142 includes a sealed opening 158.

Piston 144 includes a head 160 and an arm 162 extending from piston head 160. One end 164 of piston arm 162 is configured to couple to gantry 12 (FIG. 1). Piston 144 is positioned in hydraulic cylinder 142 so that piston arm 162 extends substantially coaxially with hydraulic cylinder 142. More particularly, piston head 160 has a substantially cylindrical geometric shape and is positioned in chamber 156 so that piston arm 162 extends through opening 158 in hydraulic cylinder first end 150.

Reservoir 146 is configured to retain a hydraulic fluid, and a fluid line 166 couples reservoir 146 to hydraulic cylinder 142. Particularly, fluid line 166 facilitates the flow of hydraulic fluid between reservoir 146 and hydraulic cylinder 142. Valves 148A and 148B are hydraulically connected in parallel circuit connection within fluid line 166 between reservoir 146 and hydraulic cylinder 142 for controlling the flow of hydraulic fluid between reservoir 146 and hydraulic cylinder 142. Valves 148A and 148B each are configured to alternate between an open position and a closed position. When either valve 148A and 148B is in the open position, hydraulic fluid flows between reservoir 146 and cylinder chamber 146. When both valves 148A and 148B is in the closed position, however, closed valves 148A and 148B, respectively, substantially prevents hydraulic fluid from flowing between reservoir 146 and hydraulic cylinder chamber 146.

FIG. 8 is a side elevation view of a hydraulic brake assembly 170 in accordance with yet another embodiment of the present invention. Brake assembly 170 includes a hydraulic cylinder 172, a piston 174, first and second reservoirs 176A and 176B, and first and second valves 178A and 178B. Hydraulic cylinder 172 includes a first end 180, a second end 182, and a sidewall 184 extending between first end 180 and second end 182 to define a chamber 186. First end 180 of hydraulic cylinder 172 includes a sealed opening 188.

Piston 174 includes a head 190 and an arm 192 extending from piston head 190. One end 194 of piston arm 192 is configured to couple to gantry 12 (FIG. 1). Piston 174 is positioned in hydraulic cylinder 172 so that piston arm 192 extends substantially coaxially with hydraulic cylinder 172. More particularly, piston head 190 has a substantially cylindrical geometric shape and is positioned in chamber 186 so that piston arm 192 extends through opening 188 in hydraulic cylinder first end 180.

Each reservoir 176A and 176B is configured to retain a hydraulic fluid, and a first fluid line 196A couples first reservoir 176A to hydraulic cylinder 172 and a second fluid line 196B couples second reservoir 176B to hydraulic cylinder 172. Particularly, first fluid line 196A facilitates the flow of hydraulic fluid between first reservoir 176A and hydraulic cylinder 172, and second fluid line 196B facilitates the flow of hydraulic fluid between second reservoir 176B and hydraulic cylinder 172. First valve 178A is connected in a series circuit connection between first reservoir 176A and hydraulic cylinder 172 for controlling the flow of hydraulic fluid in fluid line 196A between first reservoir 176A and hydraulic cylinder 172. Similarly, second valve 178B is in a series circuit connection between second reservoir 176B and hydraulic cylinder 172 for controlling the flow of hydraulic fluid in fluid line 196B between second reservoir 176B and hydraulic cylinder 172. Valves 178A and 178B each are configured to alternate between an open position and a closed position. When valve 178A is in the open position, hydraulic fluid flows between reservoir 176A and cylinder chamber 186. Similarly, when valve 178B is in the open position, hydraulic fluid flows between reservoir 176B and cylinder chamber 186. When valve 178A is in the closed position, however, closed valve 178A substantially prevents hydraulic fluid from flowing between reservoir 176A and hydraulic cylinder chamber 186. Similarly, when valve 178B is closed, hydraulic fluid is substantially prevented from flowing between reservoir 176B and hydraulic cylinder chamber 186.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. For example, the CT system described herein is a "third generation" system in which both the x-ray source and detector rotate with the gantry. Many other CT systems including "fourth generation" systems wherein the detector is a full-ring stationary detector and only the x-ray source rotates with the gantry, may be used. Similarly, while control logic is used to open and close valve 58, valve 58 may be open and closed manually. Accordingly, the spirit and scope of the invention are to be limited only by the terms of the appended claims.

What is claimed is:

1. A hydraulic brake assembly for a gantry of a computed tomography system, said brake assembly comprising:
   a hydraulic cylinder comprising a chamber;
   a piston comprising a head and an arm extending from said piston head, said piston head positioned in said hydraulic cylinder chamber so that said piston arm extends substantially coaxially with said hydraulic cylinder, said piston arm configured to couple to the gantry and serve as a brake to stabilize the gantry at a desired tilt angle;

a first reservoir configured to retain a hydraulic fluid; and a fluid line coupling said reservoir to said hydraulic cylinder for facilitating hydraulic fluid flow between said chamber and said first reservoir.

2. A hydraulic brake assembly in accordance with claim 1 wherein said piston arm is further configured to serve as a stabilizer for the gantry.

3. A hydraulic brake assembly in accordance with claim 1 further comprising a first valve positioned in said fluid line and connected in series circuit between said first reservoir and said hydraulic cylinder, said valve configured to prevent hydraulic fluid from flowing between said first reservoir and said hydraulic cylinder chamber.

4. A hydraulic brake assembly in accordance with claim 3 further comprising a second valve, said second valve in parallel circuit connection with said first valve between said first reservoir and said hydraulic cylinder.

5. A hydraulic brake assembly in accordance with claim 3 further comprising a second reservoir, a second valve, and a second fluid line, said second fluid line coupling said second reservoir to said hydraulic cylinder chamber, said second valve connected in series circuit between said second reservoir and said hydraulic cylinder, and said second valve configured to prevent hydraulic fluid from flowing between said second reservoir and said hydraulic cylinder chamber.

6. A hydraulic brake assembly in accordance with claim 3 further comprising an accumulator connected in series circuit between said valve and said hydraulic cylinder.

7. A hydraulic brake assembly in accordance with claim 3 further comprising a shock arrestor connected in series circuit between said hydraulic cylinder and said valve.

8. A hydraulic brake assembly in accordance with claim 3 further comprising a flow limiter connected in series circuit between said valve and said hydraulic cylinder.

9. A hydraulic brake assembly in accordance with claim 8 wherein said flow limiter comprises a check valve.

10. A hydraulic brake assembly in accordance with claim 3 wherein said valve is a solenoid valve.

11. A hydraulic brake assembly in accordance with claim 1 wherein said piston arm is coupled to said gantry.

12. A method for stabilizing a gantry of a computed tomography at a desired tilt angle with a brake assembly, the brake assembly coupled to the gantry and including a hydraulic cylinder having a chamber therein, a piston, a first reservoir for retaining hydraulic fluid, a fluid line coupling the first reservoir to the hydraulic cylinder, and a first valve positioned in the fuel line and connected in series circuit between the first reservoir and the hydraulic cylinder, said method comprising the steps of:

opening the valve to facilitate hydraulic fluid flow between the first reservoir and the hydraulic cylinder; [and]

tilting the pantry to the desired tilt angle; and closing the valve to prevent hydraulic fluid from flowing between the first reservoir and the hydraulic cylinder chamber to stabilize the pantry at the desired tilt angle.

13. A method in accordance with claim 12 wherein control logic is utilized to open the valve.

14. A method in accordance with claim 12 wherein control logic is utilized to close the valve.

15. A method in accordance with claim 12 wherein closing the valve comprises the step of manually closing the valve.

16. A method in accordance with claim 12 wherein opening the valve comprises the step of manually opening the valve.

17. A system comprising a tiltable gantry and a brake assembly, said brake assembly coupled to said gantry and configured to stabilize the gantry at a desired tilt angle, said brake assembly comprising:

a hydraulic cylinder comprising a chamber;

a piston comprising a head and an arm extending from said piston head, said piston head positioned in said hydraulic cylinder chamber so that said piston arm extends substantially coaxially with said hydraulic cylinder;

a first reservoir configured to retain a hydraulic fluid; and a fluid line coupling said reservoir to said hydraulic cylinder for facilitating hydraulic fluid flow between said chamber and said first reservoir.

18. A system in accordance with claim 17 wherein said brake assembly further comprises a first valve positioned in said fuel line and connected in series circuit between said first reservoir and said hydraulic cylinder, said valve configured to prevent hydraulic fluid from flowing between said first reservoir and said hydraulic cylinder chamber.

19. A system in accordance with claim 18 wherein said brake assembly further comprises a second valve, said second valve in parallel circuit connection with said first valve between said first reservoir and said hydraulic cylinder.

20. A system in accordance with claim 18 wherein said piston arm is coupled to said gantry.

* * * * *